(12) United States Patent
Tanhehco et al.

(10) Patent No.: US 8,839,812 B2
(45) Date of Patent: Sep. 23, 2014

(54) SURGICAL SUCTION FLOOR MAT

(71) Applicant: DeRoyal Industries, Inc., Powell, TN (US)

(72) Inventors: Benny Tanhehco, Powell, TN (US); Lee Freeman, Knoxville, TN (US); Joshua Garvey, Knoxville, TN (US); Mark Justice, Powell, TN (US); Craig Fernandes, Knoxville, TN (US)

(73) Assignee: DeRoyal Industries, Inc., Powell, TN (US)

( * ) Notice: Subject to any disclaimer, the term of this patent is extended or adjusted under 35 U.S.C. 154(b) by 0 days.

(21) Appl. No.: 13/743,681

(22) Filed: Jan. 17, 2013

(65) Prior Publication Data

US 2014/0196805 A1    Jul. 17, 2014

(51) Int. Cl.
  *E03B 7/08* (2006.01)
  *B65D 90/24* (2006.01)
  *A61M 1/00* (2006.01)

(52) U.S. Cl.
  CPC ................... *A61M 1/0056* (2013.01)
  USPC ............. 137/312; 222/108; 604/356

(58) Field of Classification Search
  USPC ............ 137/312; 220/571, 573; 222/108; 604/356
  See application file for complete search history.

(56) References Cited

U.S. PATENT DOCUMENTS

| | | |
|---|---|---|
| 4,533,352 A | 8/1985 | Van Beek et al. |
| 4,635,913 A | 1/1987 | Rothman |
| 4,729,404 A | 3/1988 | Hergenroeder |
| 4,765,670 A | 8/1988 | Jackson |
| 5,176,667 A * | 1/1993 | DeBring ............... 604/356 |
| 5,437,651 A | 8/1995 | Todd et al. |
| 5,628,735 A | 5/1997 | Skow |
| 5,827,246 A | 10/1998 | Bowen |
| 6,102,073 A | 8/2000 | Williams |

(Continued)

FOREIGN PATENT DOCUMENTS

GB    2466667 A    7/2010

OTHER PUBLICATIONS

International Search Report and Written Opinion, PCT/US2013/068458, date of mailing Mar. 10, 2014—11 pages.

*Primary Examiner* — Kevin Lee
(74) *Attorney, Agent, or Firm* — Luedeka Neely Group, PC

(57) ABSTRACT

A surgical suction mat for collecting and evacuating surgical fluids, the mat including a foam body having a surrounding border; a series of grooves defined on a first portion of the foam body and located interior of the border and defined substantially across the foam body, the grooves uniformly increasing in depth from adjacent a first side of the border of the foam body to a location adjacent an opposite second side of the border of the foam body, the grooves each being closed at a first end proximate the first side of the foam body and open an opposite second end; a plurality of spaced apart upper surfaces in-between the grooves and being of substantially uniform elevation to permit a relatively uniform and level upper mat surface on which a user can stand; a collection channel defined on a second portion of the foam body, the channel extending substantially perpendicular across the grooves, the collection channel being closed at each end and along one side of its length and the other side of the channel being open to and in flow communication with the grooves; and a suction fitting in fluid communication with the channel and placeable in flow communication with a source of suction to evacuate fluids from the channel through the suction fitting.

9 Claims, 11 Drawing Sheets

(56) References Cited

U.S. PATENT DOCUMENTS

| | | |
|---|---|---|
| 6,235,009 B1 | 5/2001 | Skow |
| 6,245,697 B1 | 6/2001 | Conrad et al. |
| 6,290,685 B1 | 9/2001 | Insley et al. |
| 6,531,206 B2 | 3/2003 | Johnston et al. |
| 6,532,618 B2 | 3/2003 | Koch |
| 6,568,419 B1 | 5/2003 | Robinson et al. |
| D480,805 S | 10/2003 | Thornbury et al. |
| 6,637,453 B2 | 10/2003 | Robinson |
| 6,746,567 B2 | 6/2004 | Johnston et al. |
| 6,938,639 B1 | 9/2005 | Robinson |
| 6,941,703 B2 * | 9/2005 | MacLean et al. ............ 137/312 |
| 7,051,748 B2 | 5/2006 | VanBasten |
| 7,086,409 B2 | 8/2006 | Robinson |
| 7,124,772 B1 | 10/2006 | Browning |
| 7,131,965 B1 | 11/2006 | Thornbury et al. |
| 7,291,376 B1 | 11/2007 | Siegel et al. |
| 7,316,834 B2 | 1/2008 | Hernandez |
| 7,386,957 B2 | 6/2008 | Duffney |
| 7,785,692 B1 | 8/2010 | Siegel et al. |
| 8,372,506 B2 * | 2/2013 | Vainshtein ............ 137/312 |
| 8,663,782 B1 | 3/2014 | Siegel et al. |
| 2009/0144903 A1 | 6/2009 | Delvaux et al. |

* cited by examiner

SURGICAL SUCTION FLOOR MAT

FIELD

This disclosure relates to the field of surgical floor mats. More particularly, the disclosure relates to a simplified construction for a surgical floor mat configured to be comfortable to stand on for extended periods of time, to contain and route surgical fluids against spillage onto the floor, and to connect to a source of negative pressure for evacuation of fluids from the mat.

BACKGROUND

Improvement is desired in the construction of surgical suction floor mats. Because surgical floor mats are single use in nature, it is desired to reduce the cost of such floor mats by providing a design that is uncomplicated, yet provides the desired qualities of being comfortable to stand on for extended periods of time, being configured to contain and route surgical fluids against spillage onto the floor, and being configured to connect to a source of negative pressure for evacuation of fluids from the mat.

The present disclosure relates to a surgical suction floor mat of simplified construction.

SUMMARY

The disclosure relates to a surgical suction floor mat for collecting and evacuating surgical fluids.

In one aspect, the mat includes a foam body having a surrounding border and a series of grooves defined on a first portion of the foam body. The grooves are located interior of the border and defined substantially across the foam body. The grooves uniformly increase in depth from adjacent a first side of the border of the foam body to a location adjacent an opposite second side of the border of the foam body, the grooves each being closed at a first end proximate the first side of the foam body and open an opposite second end;

A plurality of spaced apart upper surfaces are in-between the grooves and are of a substantially uniform elevation to permit a relatively uniform and level upper mat surface on which a user can stand. A collection channel is defined on a second portion of the foam body, the channel extending substantially perpendicular across the grooves, the collection channel being closed at each end and along one side of its length and the other side of the channel being open to and in flow communication with the grooves.

A suction fitting is in fluid communication with the channel and placeable in flow communication with a source of suction to evacuate fluids from the channel through the suction fitting.

The disclosure advantageously enables lightweight disposable surgical suction mats having simplified construction with a relatively uniform and level upper surface on which the user can stand.

BRIEF DESCRIPTION OF THE DRAWINGS

Further advantages of the disclosure are apparent by reference to the detailed description when considered in conjunction with the figures, which are not to scale so as to more clearly show the details, wherein like reference numbers indicate like elements throughout the several views, and wherein.

DETAILED DESCRIPTION

Figure 1:
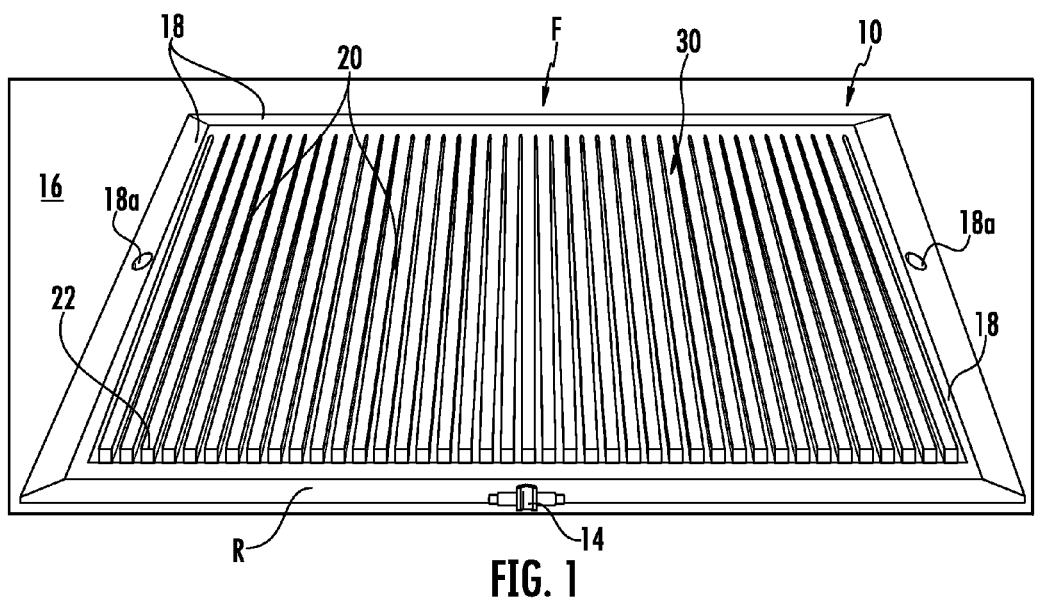
FIG. 1 is a perspective view showing a suction mat according to the disclosure.
Figure 2:
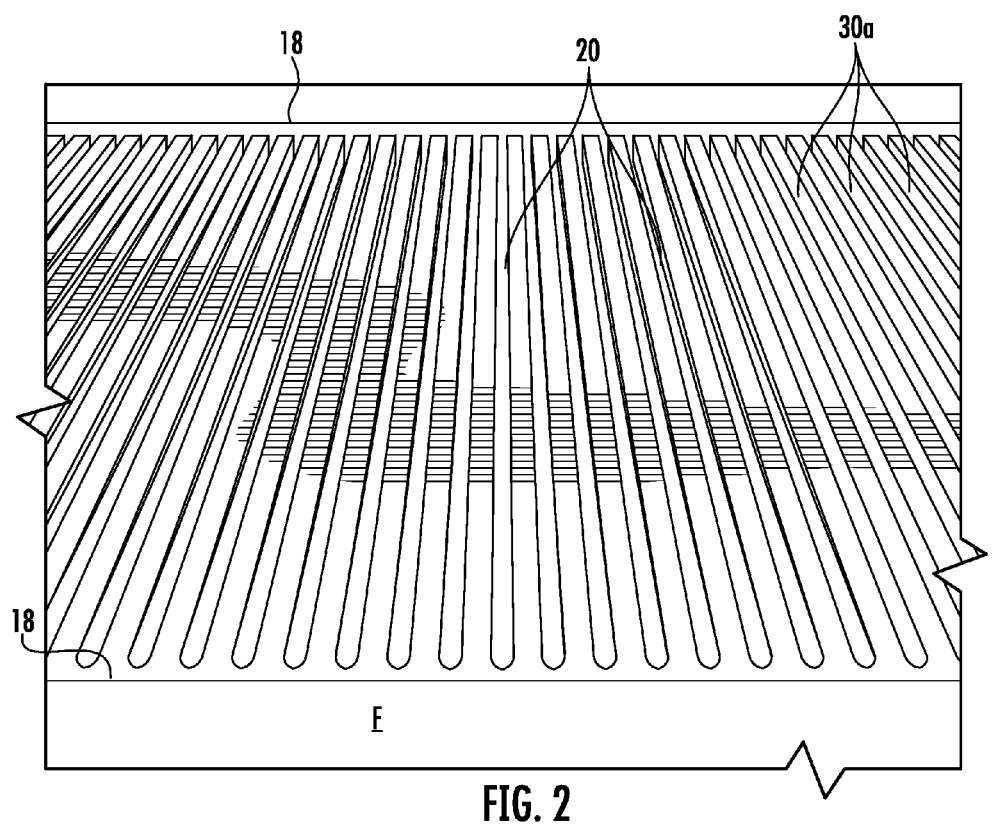
FIG. 2 shows an upper surface of the mat of FIG. 1.
Figure 3:
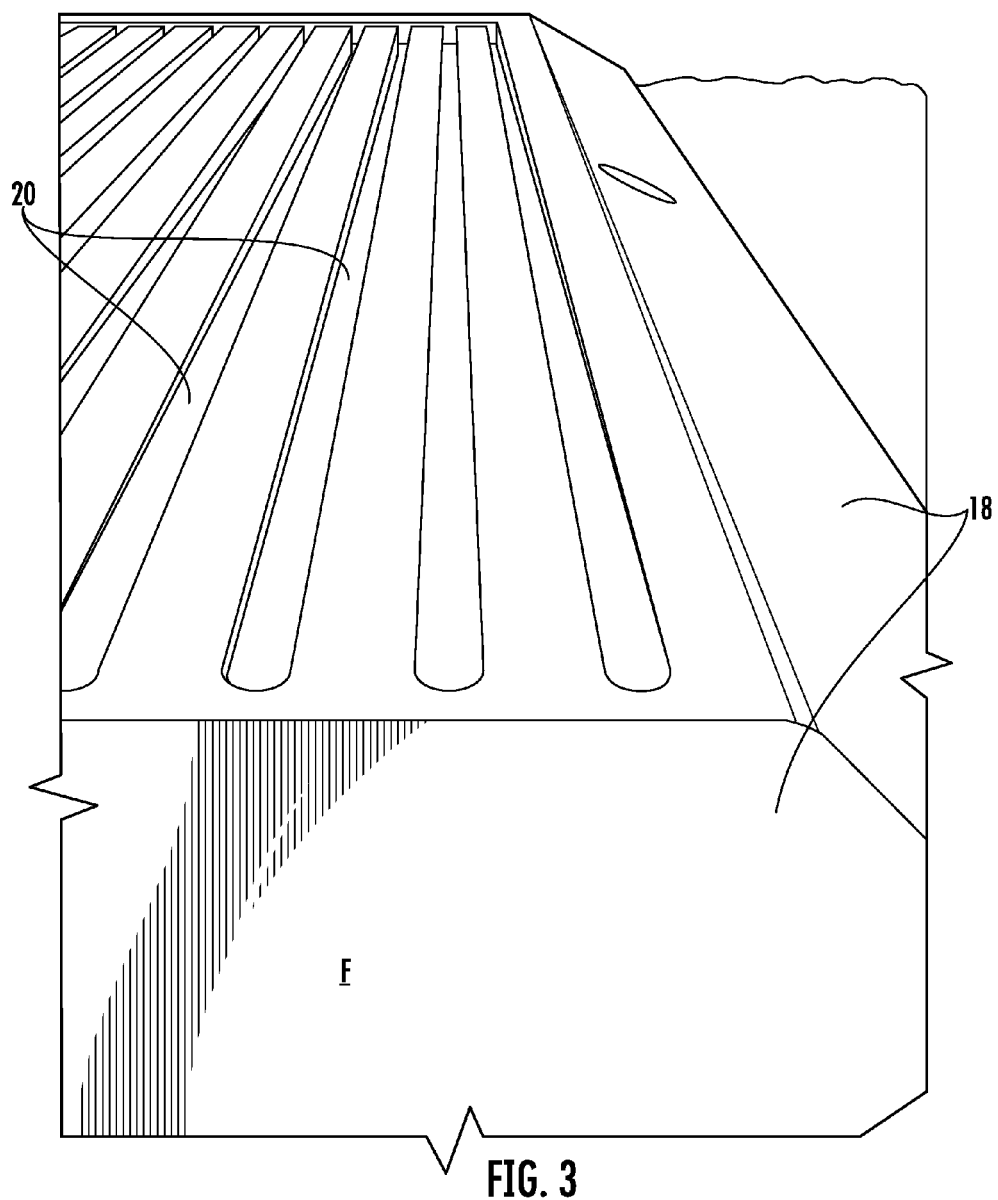
FIG. 3 is a close-up view of a front corner of the mat of FIG. 1.

With reference to the drawings, there is shown a surgical suction floor mat 10 according to the disclosure. The mat 10 includes a foam body 12 and a suction fitting 14. If desired, an absorbent surgical drape 16 may be secured underneath and extend outward from the mat 10

The foam body 12 may be made of a foam material such as a closed cell polyurethane foam. The foam body 12 is preferably substantially fluid impermeable. The foam body 12 is preferably of one-piece molded construction. However, the body 12 may be made of multiple foam pieces adhered together. The foam body 12 is substantially rectangular and has a surrounding border 18 having apertures 18a that may be used for carrying or for hanging the mat 12 for storage. A series of grooves 20 are located interior of the border 18 and defined across a dimension of the mat, such as in a direction from a front F of the body 12 to a rear R of the body 12.

Figure 4:
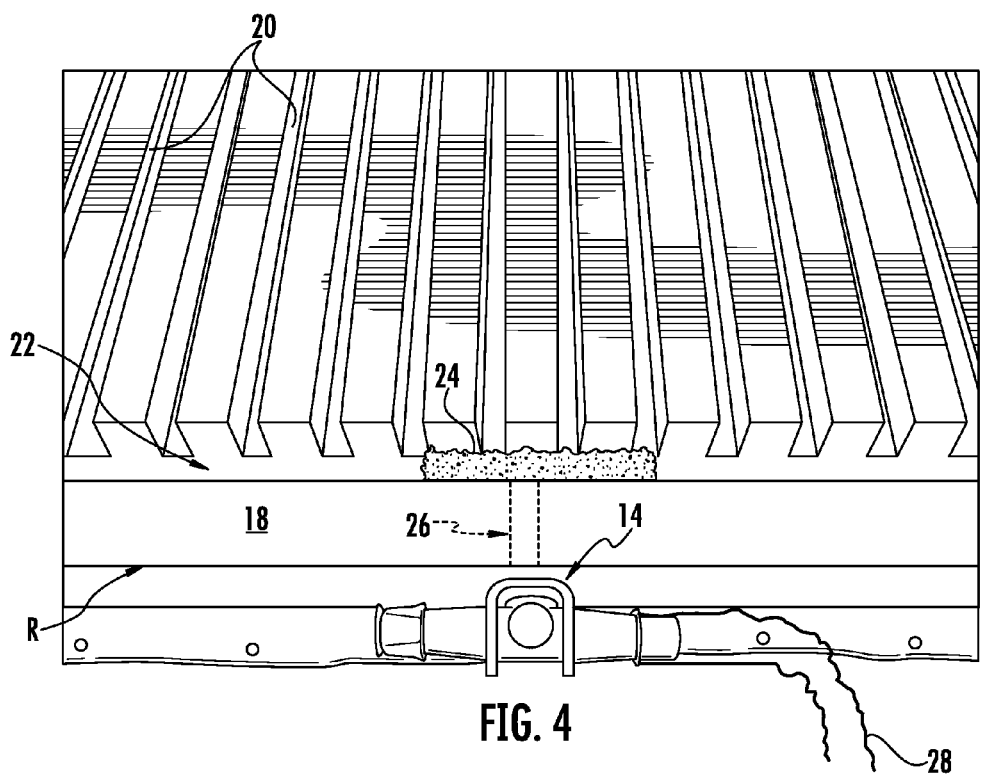
FIG. 4 is a close-up view of a rear portion of the mat of FIG. 1 having a suction fitting thereon.

The grooves 20 uniformly increase in depth from the front F to the rear R of foam body 12. That is, the grooves 20 are very shallow adjacent the front F and deepen toward the rear R so that each groove 20 provides a sloped drain surface 20a that slopes from the front F of the mat 10 toward the rear R of the mat 10. The grooves 20 are closed at their proximal end adjacent the border 18 at the front F of the body 12 and are open at their opposite terminal ends where they are the deepest, and terminate at a collection channel 22 that extends substantially perpendicular across the grooves 20 (FIG. 4). The channel 22 has a depth corresponding to at least the maximum depth of the grooves 20 and is closed at each end and along one side of its length by the border 18 and the other side of the channel 22 is open to the grooves 20.

The grooves preferably have a substantially uniform width of about 0.25 inches. The depth of the grooves 20 preferably uniformly taper from a depth of about 0.125 inches to about 0.75 inches over the length of the grooves, which length preferably is about 18 inches. Thus, the ratio of change in depth of the grooves to the length of the grooves is about 0.03.

The suction fitting 14 may be a suction T-fitting and may include a filter 24. The filter 24 is preferably a foam filter made of a large pore side open cell polyurethane foam, known as a reticulated foam. The suction fitting 14 extends through an opening 26 through the border 18 at the rear side of the body 12 opposite the channel 22 and is in flow communication with the channel 22. Surgical fluids travel via the grooves 20 to the channel 22 where they are evacuated by suction through the suction fitting 14 and a suction line 28 connected thereto.

The material in-between the grooves provides spaced apart upper surfaces 30a that are of substantially uniform elevation to permit a relatively uniform and level, relative to the underying floor, upper surface 30 on which the user can stand. In this regard, the grooves 20 are preferably substantially parallel to one another. The portions of the border 18 immediately adjacent the grooves 20 have an elevation substantially corresponding to the elevation of the upper surfaces 30a in-between the grooves to further provide a uniform and level surface on which the user can stand. In this regard, the relatively narrow width of the grooves 20 is easily spanned by the sole of the shoe of a user.

The use of a reticulated foam for the filter 24 advantageously diffuses the suction force or vacuum across the surface area of the filter 24 to create multiple small flow paths in a compact filter size for the travel of liquids. It has also been observed that the provision of multiple small dimensioned flow paths advantageously reduces the noises or sounds associated with the suctioning of the fluids from the mat and also advantageously provides effective filtration of relatively large particulates in the fluid that would tend to enter the suction fitting 14 and clog the suction fitting 14 and the suction lines 28.

Figure 5:
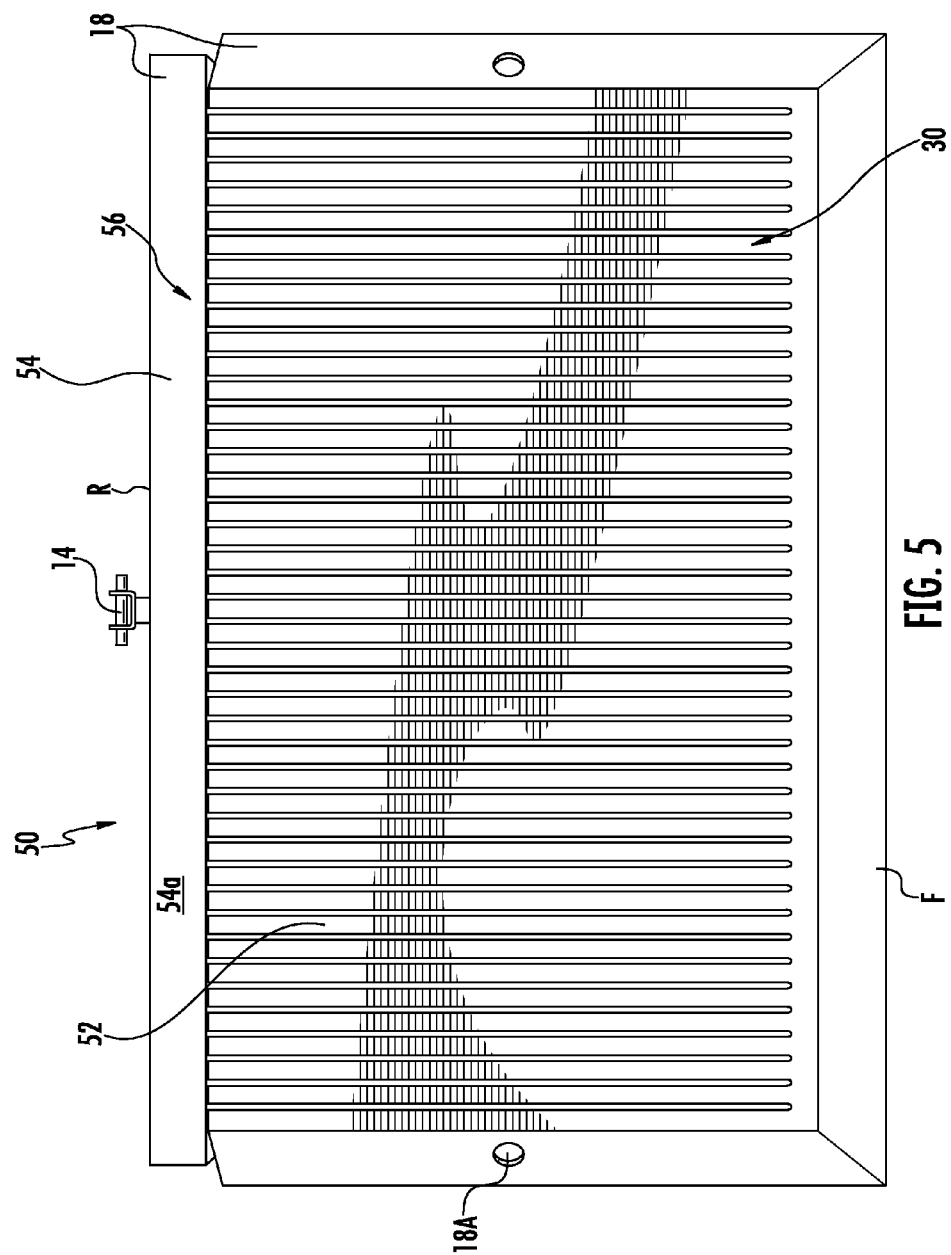
FIG. 5 is a perspective view of an alternate embodiment of a surgical suction mat according to the disclosure.
Figure 6:
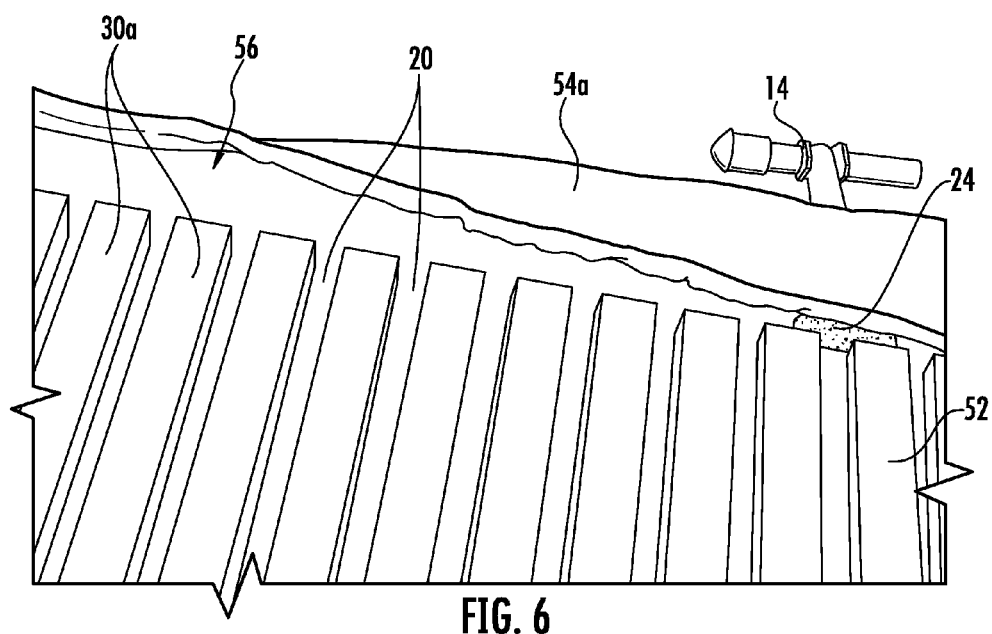
FIG. 6 is a close-up view of a rear portion of the mat of FIG. 5.
Figure 7:
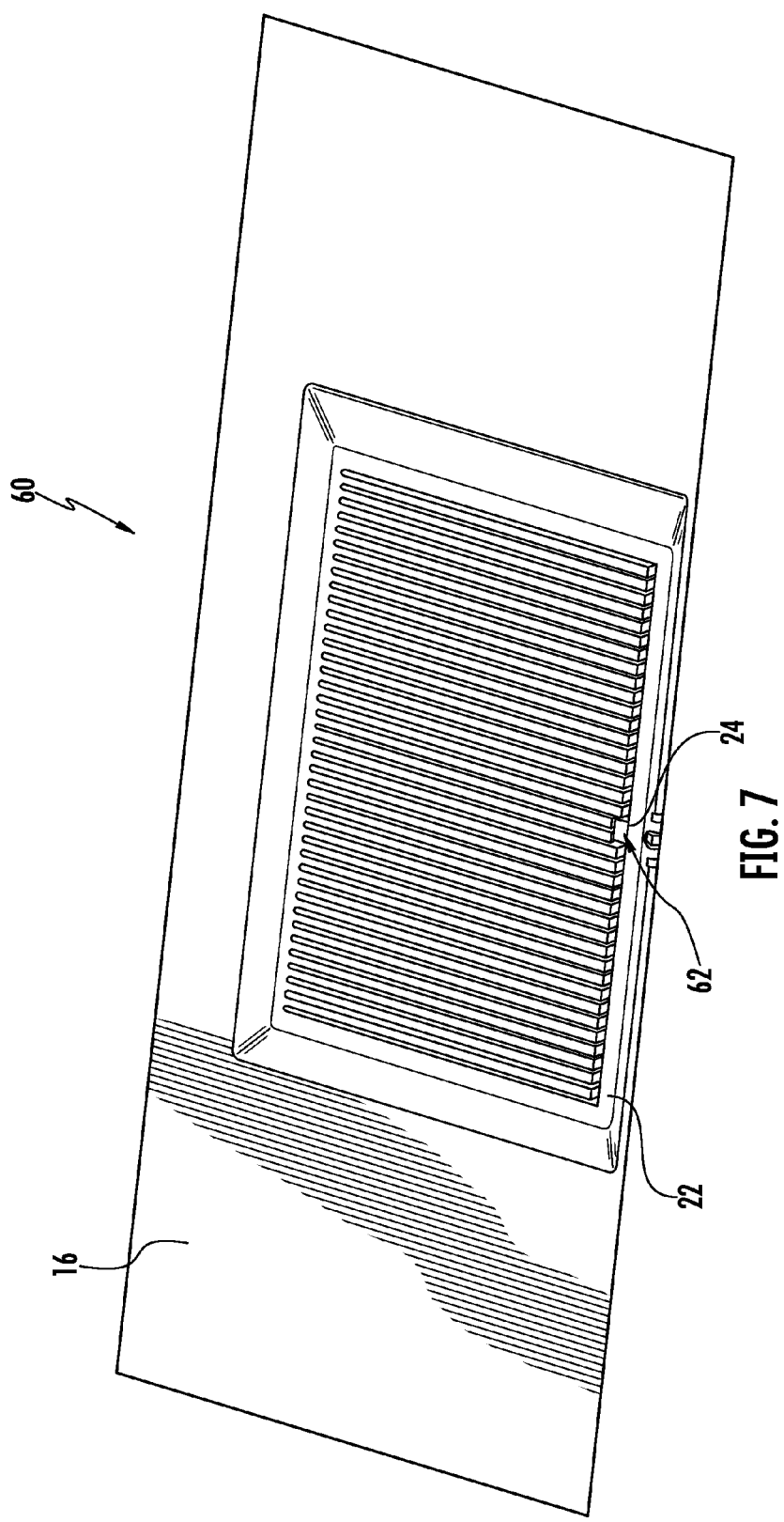
FIG. 7 is a perspective view of a further embodiment of a surgical suction mat according to the disclosure.
Figure 8:
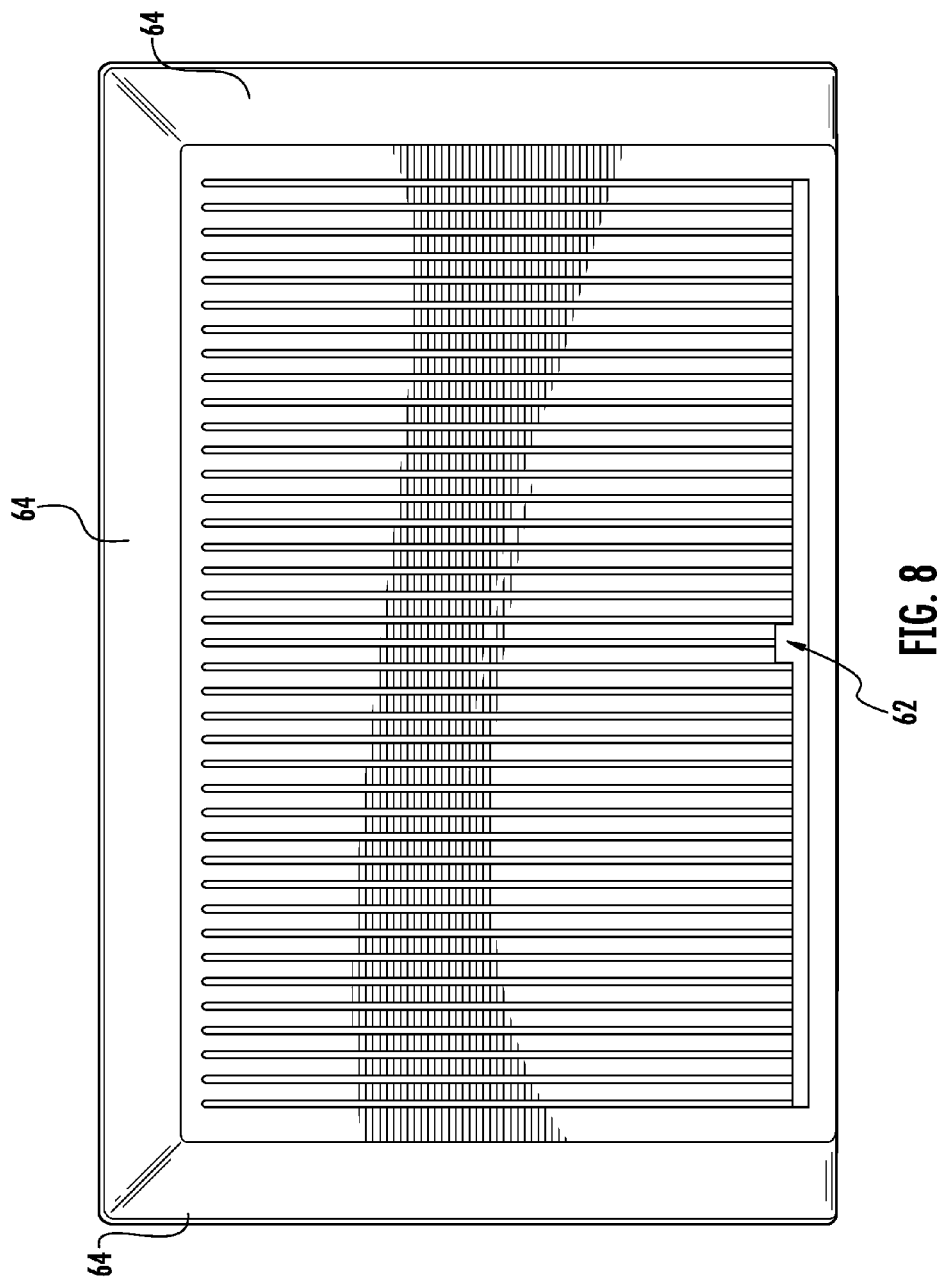
FIG. 8 is a top plan view of the mat of FIG. 7.
Figure 9:
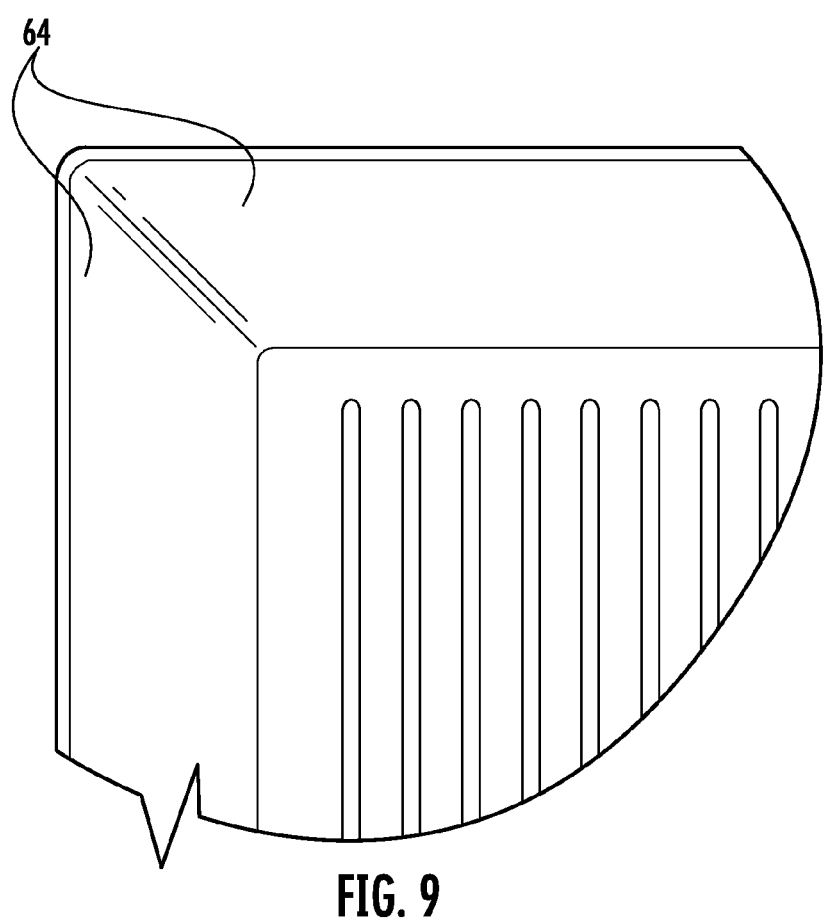
FIG. 9 is a top plan view of a corner of the mat of FIG. 7.
Figure 10:
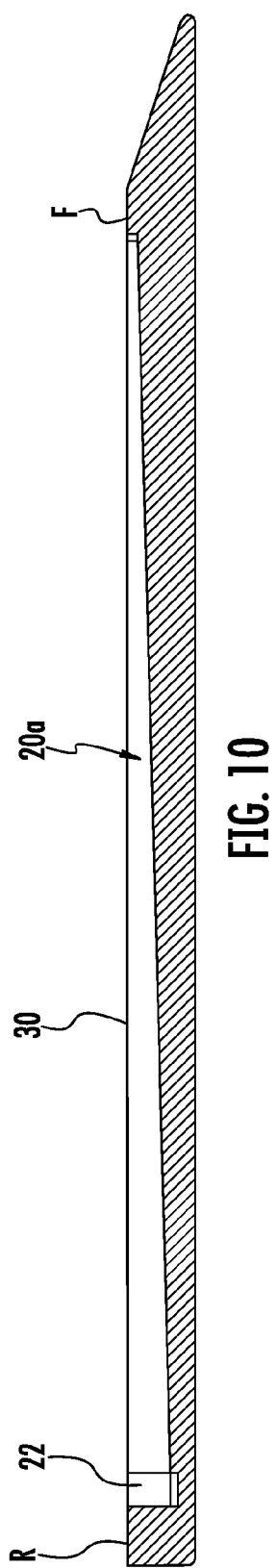
FIG. 10 is a cross-sectional side view of the mat of FIG. 7 showing front to back sloping for flow of liquid.
Figure 11:
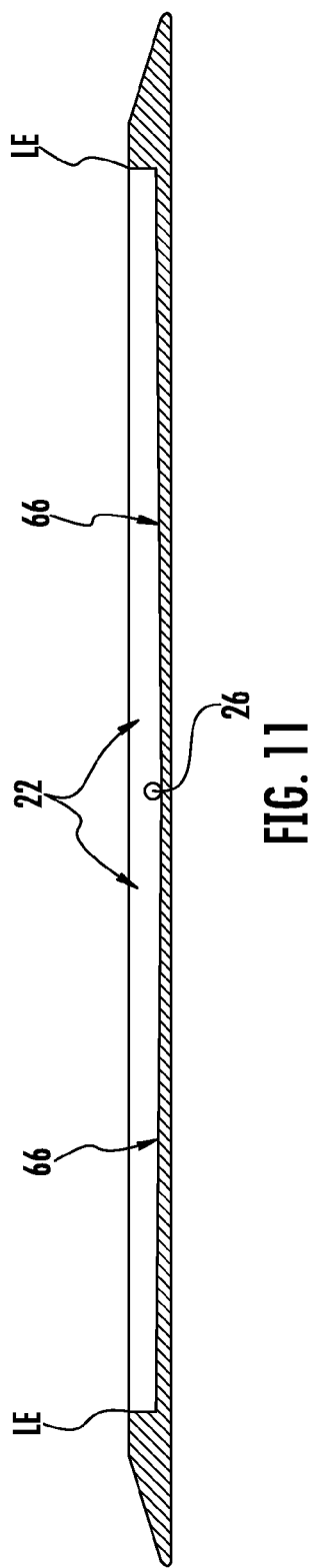
FIG. 11 is a cross-sectional end view of the mat of FIG. 7 showing side to center sloping of a collection channel of the mat for facilitating flow of liquid.

Turning to FIGS. 5 and 6, there is shown an alternate embodiment of a surgical mat 50 according to the disclosure. The mat 50 is substantially similar to the mat 10, except that it has two foam bodies 52 and 54 instead of the single foam body 12, and it has a collection channel 56 that is covered.

The foam body 52 is substantially rectangular and has a series of grooves, such as the grooves 20, defined thereon. The foam body 54 is adhesively joined to the rear of the foam body 52. The foam body 54 is generally rectangular and includes the closed end channel 56 defined along a lateral edge. When the foam body 54 is adhesively joined to the foam body 52, the channel 56 is adjacent with and in flow communication with the grooves 22.

FIG. 6 shows a covering portion 54a of the foam body pulled back so that the channel 56 can be seen. It will be understood that the foam body 54 defines part of the border 18 at the rear R of the mat 50, with the fitting 14 extending therethrough for placement in flow communication with the channel 56.

The disclosure advantageously enables lightweight disposable surgical suction mats having simplified construction with a relatively uniform and level upper surface on which the user can stand.

Turning to FIGS. 7-11, there is shown an alternate embodiment of a surgical mat 60 according to the disclosure. The mat 60 is substantially similar to the mat 10 but includes additional features.

For example, the mat 60 includes a cut out 62 in the grooves 60 proximate the filter 24 to provide additional space in the collection channel 22 at the location of the filter 24 to enable utilization of a larger sized filter 24 in the collection channel 22. This advantageously further increases the surface area of the filter and thereby further diffuse the vacuum to reduce noise.

The mat 60 also includes a construction of the edges 64 of the mat that is configured to provide a lower profile approach from the sides and rear of the mat 60. For example, the lead-in chamfer on the edges 64 is elongated to provide a lower slope angle to reduce the potential for tripping when entering the mat 60.

The mat 60 includes the grooves 20 which slope from the front F to the rear R of the mat 60 (FIG. 10), as described in connection with the mat 10 to provide the sloped drain surfaces 20a. However, in addition, the mat 60 also includes for the collection channel 22 a pair of oppositely sloped collection channel surfaces 66 that slope downward from lateral edges LE of the channel 22 to the location of the filter 24, typically centrally located on the channel 22, but, in any event, interior of the lateral edges of the channel 22. The slope from the lateral edges to the interior location of the filter 24 promotes additional gravitational flow of fluids in the channel 22 to the filter 24 for suction removal.

The foregoing description of preferred embodiments for this disclosure has been presented for purposes of illustration and description. It is not intended to be exhaustive or to limit the disclosure to the precise form disclosed. Obvious modifications or variations are possible in light of the above teachings. The embodiments are chosen and described in an effort to provide the best illustrations of the principles of the disclosure and its practical application, and to thereby enable one of ordinary skill in the art to utilize the disclosure in various embodiments and with various modifications as are suited to the particular use contemplated. All such modifications and variations are within the scope of the disclosure as determined by the appended claims when interpreted in accordance with the breadth to which they are fairly, legally, and equitably entitled.

The invention claimed is:

1. A surgical suction mat for collecting and evacuating surgical fluids, comprising:
    a foam body having a surrounding border;
    a series of grooves defined on a first portion of the foam body and located interior of the border and defined substantially across the foam body, the grooves uniformly increasing in depth from adjacent a first side of the border of the foam body to a location adjacent an opposite second side of the border of the foam body, the grooves each being closed at a first end proximate the first side of the foam body and open an opposite second end;
    a plurality of spaced apart upper surfaces in-between the grooves and being of substantially uniform elevation to permit a relatively uniform and level upper mat surface on which a user can stand;
    a collection channel defined on a second portion of the foam body, the channel extending substantially perpendicular across the grooves, the collection channel being closed at each end and along one side of its length and the other side of the channel being open to and in flow communication with the grooves; and
    a suction fitting in fluid communication with the channel and placeable in flow communication with a source of suction to evacuate fluids from the channel through the suction fitting.

2. The suction mat of claim 1, wherein the foam body is of one-piece construction.

3. The suction mat of claim 1, wherein the foam body is made of a substantially fluid impermeable foam material.

4. The suction mat of claim 1, wherein the portions of the border immediately adjacent the grooves have an elevation substantially corresponding to the elevation of the upper surfaces in-between the grooves.

5. The suction mat of claim 1, wherein the collection channel is sloped from at least one of the closed ends toward the location of the suction fitting.

6. The suction mat of claim 5, wherein the collection channel is sloped from both the closed ends toward the location of the suction fitting.

7. The suction mat of claim 5, wherein the suction fitting is located substantially centrally along the collection channel.

8. The suction mat of claim 1, wherein the suction fitting is in flow communication with a filter located within the collection channel, the filter comprising a reticulated foam filter that diffuses suction forces provided by the source of suction to reduce noises associated with suction removal of fluids and provides a plurality of reduced size flow channels which serve to filter particles in the fluid to be evacuated from entering the suction fitting.

9. The suction mat of claim 8, further comprising a cut out in the grooves proximate the filter to provide additional space in the collection channel at the location of the filter to receive a larger sized filter in the collection channel.

\* \* \* \* \*